(12) United States Patent
Jung et al.

(10) Patent No.: US 11,412,947 B2
(45) Date of Patent: Aug. 16, 2022

(54) BIO-IMPEDANCE MEASURING APPARATUS USING HALF OF UPPER BODY, BODY COMPOSITION ANALYZING APPARATUS AND BODY COMPOSITION ANALYZING METHOD

(71) Applicant: SAMSUNG ELECTRONICS CO., LTD., Suwon-si (KR)

(72) Inventors: Won Jong Jung, Seoul (KR); Kak Namkoong, Seoul (KR); Yeol Ho Lee, Anyang-si (KR); Myoung Hoon Jung, Bucheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 532 days.

(21) Appl. No.: 16/057,457

(22) Filed: Aug. 7, 2018

(65) Prior Publication Data

US 2019/0200894 A1 Jul. 4, 2019

(30) Foreign Application Priority Data

Dec. 29, 2017 (KR) .......................... 10-2017-0184331

(51) Int. Cl.
*A61B 5/0537* (2021.01)
*A61B 5/00* (2006.01)
(Continued)

(52) U.S. Cl.
CPC .......... *A61B 5/0537* (2013.01); *A61B 5/1477* (2013.01); *A61B 5/14546* (2013.01);
(Continued)

(58) Field of Classification Search
CPC ... A61B 5/0537; A61B 5/6819; A61B 5/6815; A61B 5/6822; A61B 5/6821;
(Continued)

(56) References Cited

U.S. PATENT DOCUMENTS 7,844,325 B2  11/2010  Takehara
9,258,300 B2   2/2016  Shen
(Continued)

FOREIGN PATENT DOCUMENTS

EP  3 153 099 A1  4/2017
JP  2006-215 A    1/2006
(Continued)

OTHER PUBLICATIONS

Communication dated Jan. 24, 2022 by the Korean Intellectual Property Office in Korean Patent Application No. 10-2017-0184331.
(Continued)

*Primary Examiner* — Daniel L Cerioni
*Assistant Examiner* — Raymond P Dulman
(74) *Attorney, Agent, or Firm* — Sughrue Mion, PLLC

(57) ABSTRACT

Provided is a body composition analyzing apparatus by using an impedance of a half of an upper body. According to an example embodiment, the body composition analyzing apparatus includes a first electrode part which comes into contact with a half of an upper body of an object, a second electrode part which comes into contact with the half of the upper body, a measurer configured to apply a current to each of the electrode parts, and to measure an impedance of the half of the upper body of the object by measuring a voltage of each of the electrode parts, and an analyzer configured to analyze body composition of the object based on the measured impedance of the half of the upper body.

33 Claims, 23 Drawing Sheets

(51) Int. Cl.
*A61B 5/145* (2006.01)
*A61B 5/1477* (2006.01)
*A61B 5/22* (2006.01)

(52) U.S. Cl.
CPC ............ *A61B 5/224* (2013.01); *A61B 5/4504* (2013.01); *A61B 5/4872* (2013.01); *A61B 5/4878* (2013.01); *A61B 5/6803* (2013.01); *A61B 5/6815* (2013.01); *A61B 5/6819* (2013.01); *A61B 5/6821* (2013.01); *A61B 5/6822* (2013.01); *A61B 5/6898* (2013.01); *A61B 5/7278* (2013.01); *A61B 5/742* (2013.01); *A61B 5/7405* (2013.01); *A61B 5/7455* (2013.01); *A61B 5/7475* (2013.01); *A61B 2560/0431* (2013.01); *A61B 2560/0468* (2013.01)

(58) Field of Classification Search
CPC ... A61B 5/14546; A61B 5/1477; A61B 5/224; A61B 5/4504; A61B 5/4872; A61B 5/4878; A61B 5/7278; A61B 5/7405; A61B 5/742; A61B 5/7455; A61B 5/7475; A61B 5/6898; A61B 5/6803; A61B 2560/0468; A61B 2560/0431; A61B 5/4869
See application file for complete search history.

(56) References Cited

U.S. PATENT DOCUMENTS

| | | | |
|---|---|---|---|
| 9,504,406 B2 | 11/2016 | Chetham et al. | |
| 9,579,060 B1 * | 2/2017 | Lisy | A61B 5/14551 |
| 10,244,983 B2 | 4/2019 | Shim et al. | |
| 2008/0306400 A1 | 12/2008 | Takehara | |
| 2009/0143663 A1 * | 6/2009 | Chetham | A61B 5/4878 |
| | | | 600/372 |
| 2010/0168530 A1 | 7/2010 | Chetham et al. | |
| 2010/0331660 A1 | 12/2010 | Wada et al. | |
| 2013/0245399 A1 | 9/2013 | Choi et al. | |
| 2014/0051940 A1 | 2/2014 | Messerschmidt | |
| 2014/0058220 A1 * | 2/2014 | LeBoeuf | A61B 5/021 |
| | | | 600/301 |
| 2016/0081581 A1 * | 3/2016 | Eom | A61B 5/0537 |
| | | | 600/547 |
| 2016/0089053 A1 * | 3/2016 | Lee | A61B 5/681 |
| | | | 600/384 |
| 2016/0113579 A1 | 4/2016 | Seo et al. | |
| 2016/0128604 A1 * | 5/2016 | Eom | A61B 5/065 |
| | | | 600/384 |
| 2016/0249857 A1 | 9/2016 | Choi et al. | |
| 2016/0296136 A1 * | 10/2016 | Jung | A61B 5/0537 |
| 2017/0020449 A1 | 1/2017 | Shim et al. | |
| 2017/0020454 A1 | 1/2017 | Keteyian et al. | |
| 2017/0100052 A1 | 4/2017 | Jung et al. | |
| 2017/0164878 A1 * | 6/2017 | Connor | A61B 5/053 |
| 2018/0220923 A1 | 8/2018 | Shim et al. | |
| 2019/0357804 A1 * | 11/2019 | Kingsford | A61B 5/02028 |

FOREIGN PATENT DOCUMENTS

| | | |
|---|---|---|
| JP | 2010-510835 A | 4/2010 |
| JP | 5190223 B2 | 4/2013 |
| JP | 2014-69030 A | 4/2014 |
| KR | 10-2005-0050992 A | 6/2005 |
| KR | 20-0388394 Y1 | 6/2005 |
| KR | 10-2008-0102581 A | 11/2008 |
| KR | 10-1689553 B1 | 12/2016 |
| KR | 10-2017-0010703 A | 2/2017 |
| WO | 01/76220 A1 | 10/2001 |

OTHER PUBLICATIONS

Communication dated Mar. 22, 2019 issued by the European patent office in counterpart European Patent Application No. 18194513.0.

* cited by examiner

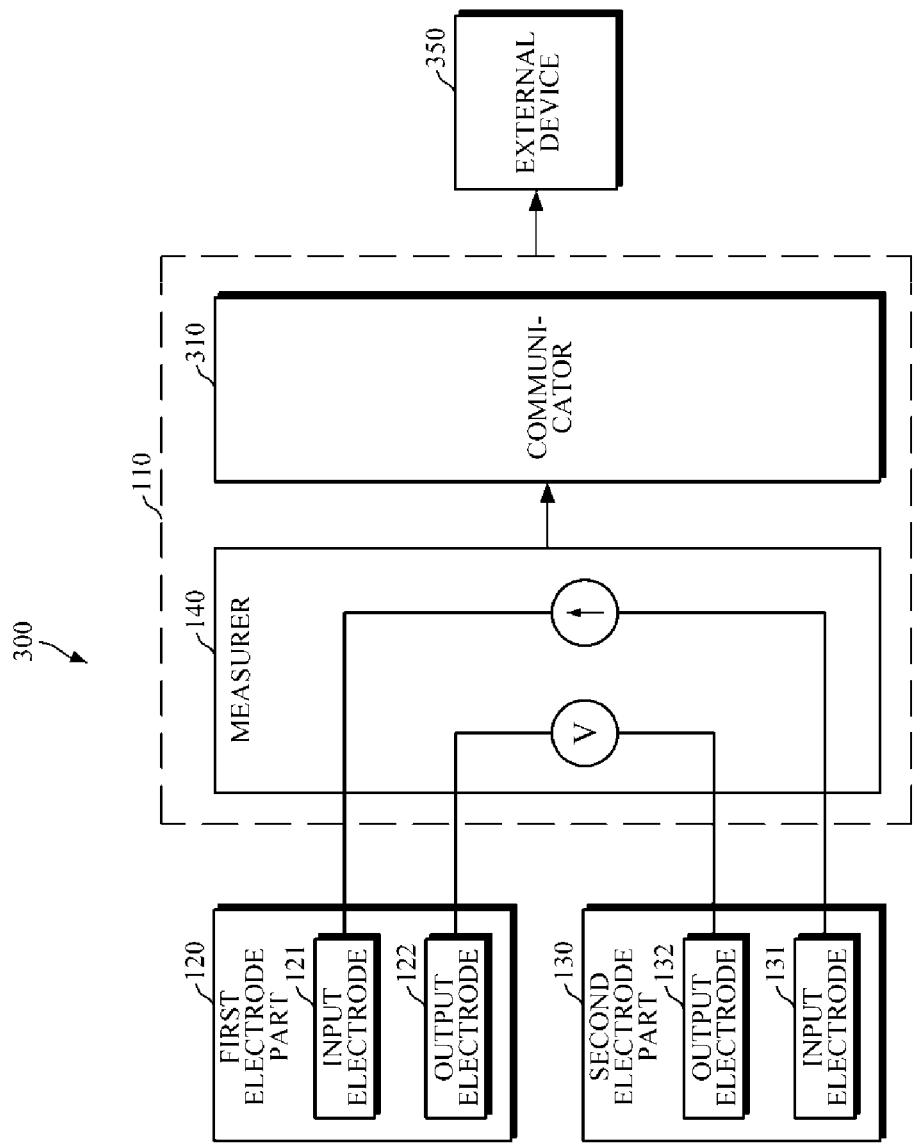

BIO-IMPEDANCE MEASURING APPARATUS USING HALF OF UPPER BODY, BODY COMPOSITION ANALYZING APPARATUS AND BODY COMPOSITION ANALYZING METHOD

CROSS-REFERENCE TO RELATED APPLICATION

This application claims priority from Korean Patent Application No. 10-2017-0184331, filed on Dec. 29, 2017 in the Korean Intellectual Property Office, the entire disclosure of which is incorporated herein by reference.

BACKGROUND

1. Field

One or more example embodiments of the present disclosure relate to a bio-impedance measuring apparatus using the half of an upper body of an object, and an apparatus and method of analyzing body composition by using the measured bio-impedance.

2. Description of the Related Art

In the past, there was less interest in body composition, and body composition was generally measured in hospitals for medical checkup. However, with a recent improvement in living standards, and a growing interest in health and diet, people's interest in measuring body composition in their daily lives and monitoring body composition changes has increased. Measuring the body composition refers to quantitative measurement of individual elements of body composition, such as water, proteins, bones, fat, and the like, which form the human body. As a method of measuring body composition, bioelectrical impedance analysis (BIA) is widely used, which is lower in cost and less harmful to humans. The BIA is a method of calculating an amount of body water, muscles, body fat, and the like, by using a value of electrical impedance, i.e., electric resistance of the human body which is obtained by applying a weak electric current to the human body, and by using information including a user's stature, weight, age, gender, and the like. As a method of measuring body composition, there is a method of measuring body composition of the whole body by using contact electrodes, which come into contact with the palms of both hands, and contact electrodes which come into contact with the soles of both feet, and a method of measuring body composition of the upper body by using contact electrodes which come into contact with the palms of both hands.

SUMMARY

One or more example embodiments provide a bio-impedance measuring apparatus using the half of an upper body of an object, and an apparatus and method of analyzing body composition by using the measured bio-impedance.

According to an aspect of an example embodiment, there is provided a body composition analyzing apparatus including a first electrode part configured to come into contact with a first portion of a half of an upper body of an object, a second electrode part configured to come into contact with a second portion of the half of the upper body, a measurer configured to apply a current to the first electrode part and the second electrode part, and to measure an impedance of the half of the upper body of the object based on measuring a voltage of the first electrode part and the second electrode part, and an analyzer configured to analyze body composition of the object based on the measured impedance of the half of the upper body.

The half of the upper body of the object may be a left half or a right half based on a left-right symmetric point of the upper body of the object.

The first electrode part may be further configured to come into contact with at least one of a face, an ear, a nose, and a neck of the half of the upper body of the object, and the second electrode part may be further configured to come into contact with a hand of the half of the upper body of the object.

The body composition analyzing apparatus may further include a main body, the main body being a mobile terminal, wherein the first electrode part is disposed on a front surface of the mobile terminal, and the second electrode part is disposed on a side surface or a rear surface of the mobile terminal.

The body composition analyzing apparatus may further include a main body, the main body being an earphone, wherein the first electrode part is disposed on an inner side surface of a neckband of the earphone which is further configured to come into contact with the ear or the neck of the half of the upper body of the object or an inner side surface of an earbud which is further configured to be inserted into the ear of the half of the upper body of the object, and wherein the second electrode part is disposed on an outer side surface of the neckband or the earbud of the earphone which is exposed to the outside or disposed at a controller of the earphone connected to the earbud of the earphone.

The body composition analyzing apparatus may further include a main body, the main body being glasses, wherein the first electrode part is disposed on an inner surface of a nose pad or temples of the glasses and is further configured to come into contact with at least one of the nose, the ear, and the face of the half of the upper body of the object, and the second electrode part is disposed on an outer surface of the glasses and is further configured to come into contact with the hand of the half of the upper body of the object.

The body composition analyzing apparatus may further include an input interface configured to receive a user input of user information comprising at least one of sex, age, height, and weight of the object.

The analyzer may be further configured to analyzes the body composition based on the input user information and the measured impedance of the half of the upper body of the object.

The body composition analyzing apparatus, wherein after the impedance of the half of the upper body is measured, the analyzer is further configured to correct the measured impedance of the half of the upper body based on at least one of an impedance of a whole body and an impedance of the upper body, and to analyze the body composition based on the corrected impedance, and wherein the impedance of the whole body and the impedance of the upper body is stored in a storage.

The analyzer may be further configured to convert the corrected impedance of the half of the upper body of the object into at least one of a linear expression, a fractional expression, and an exponential expression, and to analyze the body composition based on the converted impedance.

The analyzer may be further configured to calculate a body balance index by comparing an analysis result of body composition of a left half of the upper body with an analysis result of body composition of a right half of the upper body of the object.

The body composition may include at least one of intracellular water, extracellular water, proteins, minerals, a body fat, a skeletal muscle mass, a degree of obesity, a muscle strength, an edema, a body composition ratio, a visceral fat, a body mass index (BMI), and a skeletal mass index (SMI).

The body composition analyzing apparatus may further include an output part configured to output at least one of the measured impedance of the half of the upper body of the object and an analysis result of the body composition.

According to an aspect of another example embodiment, there is provided a body composition analyzing method including applying a current to a first electrode part and a second electrode part which are configured to come into contact with a first portion and a second portion of a half of an upper body of an object, respectively, measuring an impedance of the half of the upper body of the object based on a voltage measured of the first electrode part and the second electrode part, and analyzing body composition of the object based on the measured impedance of the half of the upper body of the object.

The first electrode part may be further configured to come into contact with at least one of a face, an ear, a nose, and a neck of the half of the upper body of the object, and the second electrode part is configured to come into contact with a hand of the half of the upper body of the object.

The analyzing of the body composition may further include analyzing the body composition based on user information comprising at least one of sex, age, height, and weight of the object, and the measured impedance of the half of the upper body of the object.

The analyzing of the body composition may further include correcting the measured impedance of the half of the upper body based on at least one of an impedance of a whole body and an impedance of the upper body, and analyzing the body composition based on the corrected impedance, and wherein the impedance of the whole body and the impedance of the upper body is stored in a storage.

The body composition analyzing method may further include outputting at least one of the measured impedance of the half of the upper body of the object and an analysis result of the body composition.

According to an aspect of another example embodiment, there is provided a bio-impedance measuring apparatus including a main body, a first electrode part which is disposed in the main body and is configured to come into contact with a half of an upper body of an object, a second electrode part which is disposed in the main body and is configured to come into contact with the half of the upper body of the object, and a measurer which is disposed in the main body and is configured to apply a current to the first electrode part and the second electrode part, and to measure an impedance of the half of the upper body of the object based on measuring a voltage of the first electrode part and the second electrode part.

The bio-impedance measuring apparatus, wherein each of the first electrode part and the second electrode part may include an input electrode, to which the current is applied, and an output electrode configured to output the voltage.

The input electrode and the output electrode may be formed in at least one of a bar shape, a semi-circular shape, and a circular shape.

The half of the upper body of the object may be a left half or a right half based on a left-right symmetric point of the upper body.

The main body may be a mobile terminal, and wherein the first electrode part is disposed on a front surface of the mobile terminal and is further configured to come into contact with a face or an ear of the half of the upper body of the object, and the second electrode part is disposed on a side surface or a rear surface of the main body and is further configured to come into contact with a hand of the half of the upper body of the object.

The bio-impedance measuring apparatus may further include a display disposed in the main body and configured to display a measurement result of the bio-impedance.

The main body may be an earphone, wherein the first electrode part is disposed on an inner side surface of a neckband of the earphone configured to come into contact with an ear or a neck of the half of the upper body of the object or an inner side surface of an earbud of the earphone which is configured to be inserted into the ear of the half of the upper body of the object, and wherein the second electrode part is disposed on an outer side surface of the neckband or the earbud of the earphone which is exposed to the outside or disposed at a controller of the earphone connected to the neckband or the earbud of the earphone to come into contact with a hand of the half of the upper body of the object.

The bio-impedance measuring apparatus, wherein when being connected by wire to an external device, the measurer may apply the current to the first electrode part and the second electrode part by receiving power from the external device.

The bio-impedance measuring apparatus may further include a communicator configured to transmit one or more of the measured voltage and the measured bio-impedance to an external device through wired or wireless communication.

The main body may be glasses, and wherein the first electrode part is disposed on an inner surface of a nose pad or temples of the glasses and is further configured to come into contact with at least one of a nose, an ear, and a face of the half of the upper body of the object, and the second electrode part is disposed on an outer surface of the temples of the glasses and is further configured to come into contact with a hand of the half of the upper body of the object.

The bio-impedance measuring apparatus may further include a display disposed on the main body and configured to display a measurement result of the bio-impedance.

The first electrode part may include a first input electrode and a first output electrode, and the second electrode part may include a second input electrode and a second output electrode, wherein the measurer is further configured apply the current to each of the first input electrode and the second input electrode, and to measure the voltage between the first output electrode and the second output electrode.

The output part may include at least one of a display, a speaker, and a haptic module.

The analyzing of the body composition may further include converting the corrected impedance of the half of the upper body of the object into at least one of a linear expression, a fractional expression, and an exponential expression, and analyzing the body composition based on the converted impedance.

According to an aspect of another example embodiment, there is provided a bio-impedance measuring apparatus including a main body, a first electrode part which is disposed in the main body and is configured to come into contact with a half of an upper body of an object, a second electrode part which is disposed in the main body and is configured to come into contact with the half of the upper body of the object, a measurer which is disposed in the main body and is configured to apply a current to the first electrode part and the second electrode part, and to measure an impedance of the half of the upper body of the object based on measuring a voltage of first electrode part and the second electrode part, and an analyzer configured to correct the measured impedance of the half of the upper body based on at least one of an impedance of a whole body and an impedance of the upper body, to convert the corrected impedance of the of the half of the upper body of the object into at least one of a linear expression, a fractional expression, and an exponential expression, and to analyze the body composition based on the converted impedance.

BRIEF DESCRIPTION OF THE DRAWINGS

The above and other aspects will become apparent and more readily appreciated from the following description of the example embodiments, taken in conjunction with the accompanying drawings in which:

FIGS. 1, 2, and 3 are block diagrams illustrating examples of a bio-impedance measuring apparatus according to an example embodiment;

DETAILED DESCRIPTION

Figure 1:
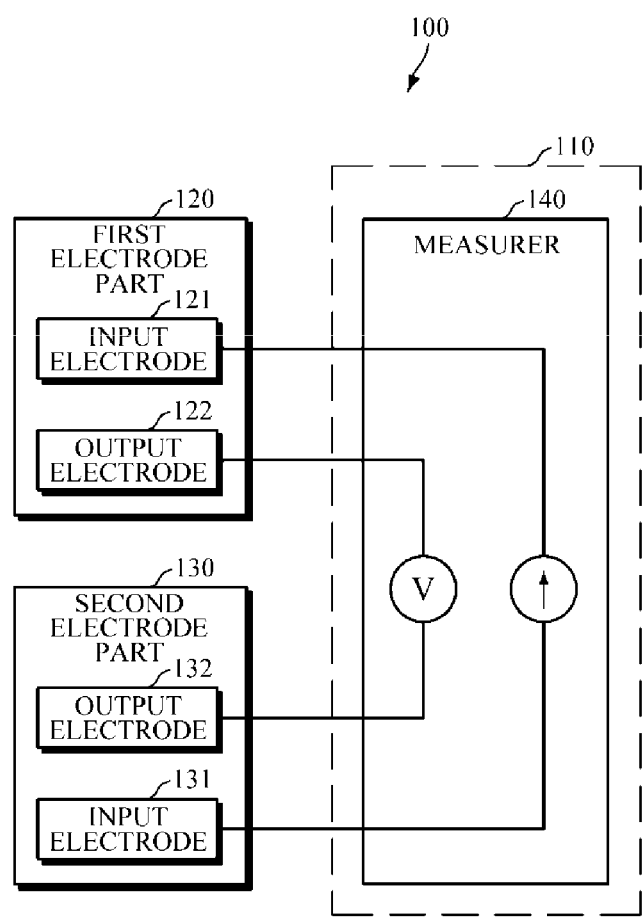

Details of example embodiments are included in the following detailed description and drawings. Advantages and features of the present disclosure, and a method of achieving the same will be more clearly understood from the following example embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., should be understood as a unit that performs at least one function or operation and that may be embodied as hardware, software, or a combination thereof.

As used herein, the term "and/or" includes any and all combinations of one or more of the associated listed items. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Hereinafter, embodiments of a bio-impedance measuring apparatus, and a body composition analyzing apparatus and body composition analyzing method, to which the bio-impedance measuring apparatus is applied, will be described in detail with reference to the accompanying drawings.

Figure 2:
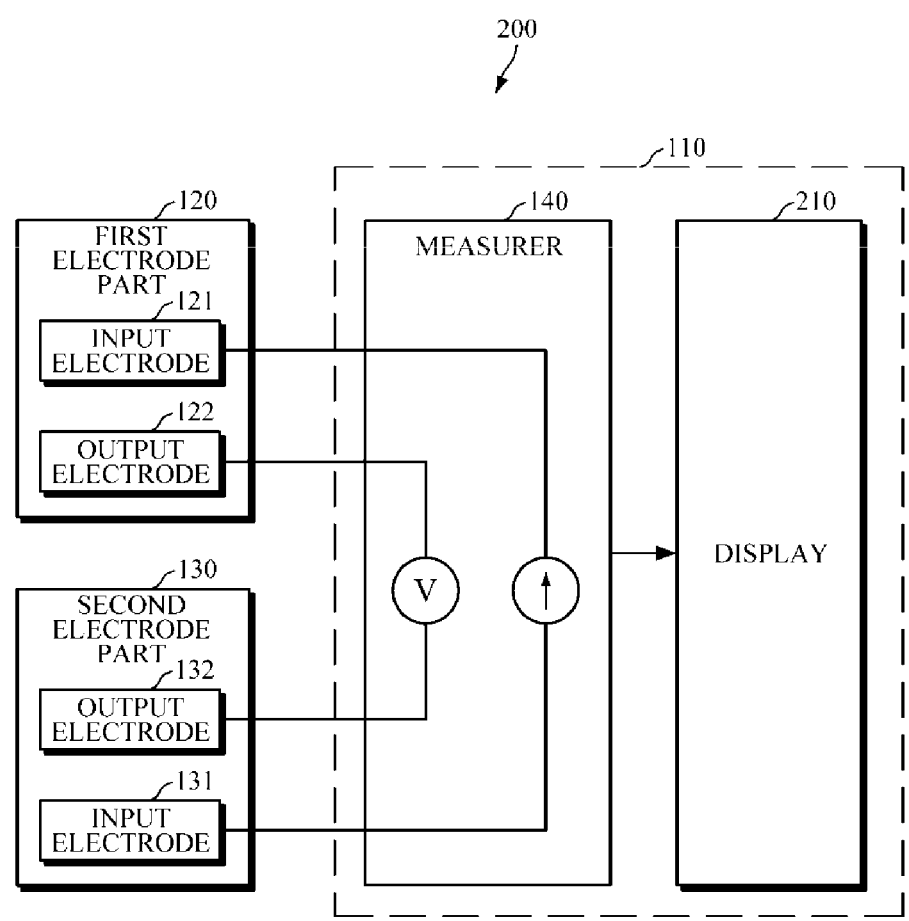

FIGS. 1 to 3 are block diagrams illustrating examples of a bio-impedance measuring apparatus according to an example embodiment.

Referring to FIG. 1, the bio-impedance measuring apparatus 100 includes a main body 110, a first electrode 120, a second electrode 130, and a measurer 140.

The first electrode 120 and the second electrode 130 are disposed at the main body 110, in such a manner that the first electrode 120 and the second electrode 130 are exposed to the outside and configured to come into contact with an object. The first electrode 120 and the second electrode 130 may measure bio-impedance by using a two-electrode method or a four-electrode method. For example, referring to FIG. 1, in order to measure bio-impedance by using a four-electrode method, the first electrode part 120 and the second electrode part 130 may be composed of a pair of an input electrode 121 and an output electrode 122 and a pair of an input electrode 131 and an output electrode 132 respectively. The input electrodes 121 and 131 and the output electrodes 122 and 132 may be formed in various shapes such as a bar shape, a semi-circular shape, a circular shape, and the like. Further, based on types of the main body 110, a position of contact with an object, and the like, the first electrode 120 and the second electrode 130 may have different shapes. For example, the first electrode part 120 may be formed in a bar shape, and the second electrode part 130 may be formed in a circular shape.

The measurer 140, which is embedded in the main body 110, may apply a current to the first electrode part 120 and the second electrode part 130, and may measure bio-impedance by measuring a voltage of the first electrode part 120 and the second electrode part 130. For example, the measurer 140 may apply an alternating current between the input electrodes 121 and 131 of the first electrode part 120 and the second electrode part 130, respectively, which are configured to be in contact with an object, and may measure bio-impedance by measuring a voltage produced between the output electrodes 122 and 132. In this case, the alternating current may be a constant current of, for example, about 500μ having a frequency of 50 kHz, but aspects of example embodiments are not limited thereto.

The measurer 140 may apply a current to the input electrodes 121 and 131 by using the power of a battery mounted in the main body 110. Alternatively, in the case where the bio-impedance measuring apparatus 100 is connected by wire to an external device, the measurer 140 may apply a current to the input electrodes 121 and 131 by using the power of the external device.

In an example embodiment, the first electrode part 120 and the second electrode part 130 may be disposed at a position of the main body 110 to contact a region of the half of an upper body of an object. For example, the first electrode part 120 may be disposed on one surface of the main body 110 and configured to be in contact with a face or an ear of the half of an upper body of the object, and the second electrode part 130 may be disposed on the other surface of the main body 110 and configured to be in contact with a hand, e.g., a finger, a palm, and other positions of the hand, of the half of the upper body of the object. For example, the half of the upper body of the object may be a left half or a right half of the upper body based on a left-right symmetric point of the upper body, for example, the solar plexus, and may include an abdomen.

The measurer 140 may measure an impedance of the half of the upper body in the region of the half of the upper body of the object, and may convert the measured impedance of the half of the upper body to an impedance of the upper body or whole body. As the upper body is left-right symmetric based on the solar plexus, the impedance of the upper body or the whole body may be measured by using the impedance of the half of the upper body.

As will be described later with reference to FIGS. 5A to 7C, the main body 110 may have various types of structures according to example embodiments. For example, the main body 110 may be of a mobile terminal type. In this case, the main body 110 may include modules which perform not only a function of measuring bio-impedance, but also original functions of a mobile terminal. In another example, the main body 110 may be of a glasses-type or a virtual reality (VR) device type. In this case, the main body 110 may include modules to perform functions of a glasses-type wearable device or a VR device. In another example, the main body 110 may be of an earphone type. In this case, examples of the earphone types may include terminal type earphones, neckband type earphones, Bluetooth earphones, bone-conduction earphones, headphones, and the like, and various modules to perform functions of each type of earphones may be further mounted in the main body 110.

Referring to FIG. 2, the bio-impedance measuring apparatus 200 may further include a display 210, in addition to the main body 110, the first electrode part 120, the second electrode part 130, and the measurer 140. The main body 110, the first electrode part 120, the second electrode part 130, and the measurer 140 are described above with reference to FIG. 1, such that detailed description thereof will be omitted.

The display 210 may be mounted in the main body 110, and once the bio-impedance of the half of the upper body is measured by the measurer 140, the display 210 may output the measured bio-impedance. The display 210 may be included according to the types of the main body 110. The display 210 may output the measured bio-impedance in various visual methods. The display 210 may output a history of bio-impedance measurements in the form of a graph and the like, to enable a user to more easily analyze the history of bio-impedance measurements.

Further, while the bio-impedance of the half of the upper body is measured, the display 210 may display an outline of the half of the upper body, the bio-impedance of which is measured, and may display a contact position of the first electrode part 120 and the second electrode part 130 on the outline of the half of the upper body.

Referring to FIG. 3, the bio-impedance measuring apparatus 200 may further include a communicator 310, in addition to the main body 110, the first electrode part 120, the second electrode part 130, and the measurer 140. The main body 110, the first electrode part 120, the second electrode part 130, and the measurer 140 are described above with reference to FIG. 1, such that detailed description thereof will be omitted.

The communicator 310 may be connected to an external device 350 by using wired or wireless communication techniques. In this case, the external device 350 may be a device which may receive the bio-impedance measured by the bio-impedance measuring apparatus 300, and may analyze body composition by using the received bio-impedance. For example, the external device 350 may include a smartphone, a tablet personal computer (PC), a desktop computer, a laptop computer, and the like, and may be various types of wearable devices such as a wrist-type wearable device, a hair band-type wearable device, and the like.

Once the bio-impedance of the half of the upper body is measured, the communicator 130 may transmit the measured bio-impedance of the half of the upper body to the external device 350. Further, the communicator 310 may receive a control signal for measuring the bio-impedance of the half of the upper body from the external device 350, and may transmit the received control signal to the measurer 140.

In this case, examples of the wireless communication techniques may include Bluetooth communication, Bluetooth Low Energy (BLE) communication, near field communication (NFC), wireless local area network (WLAN) communication, Zigbee communication, infrared data association (IrDA) communication, Wi-Fi Direct (WFD) communication, ultra-wideband (UWB) communication, Ant+ communication, Wi-Fi communication, radio frequency identification (RFID) communication, 3G communication, 4G communication, 5G communication, and the like, but is not limited thereto.

Figure 4A:
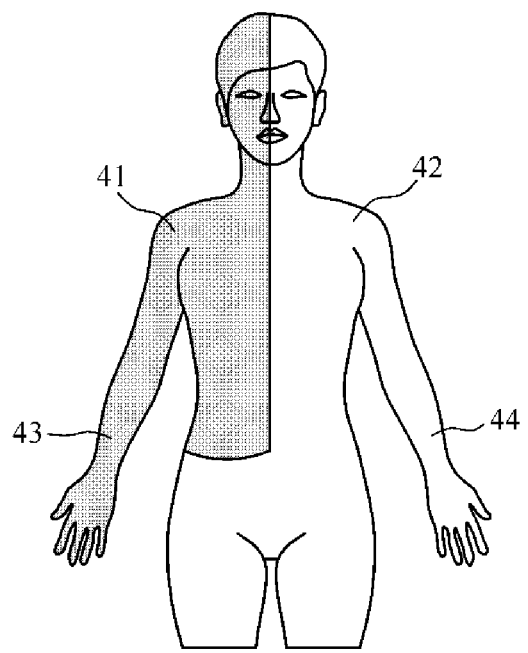
FIGS. 4A, 4B, and 4C are diagrams explaining an example of measuring bio-impedance of a half of an upper body according to an example embodiment.
Figure 4B:
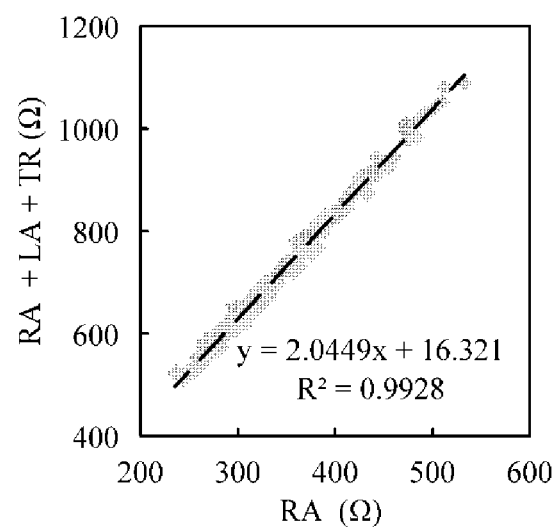
Figure 4C:
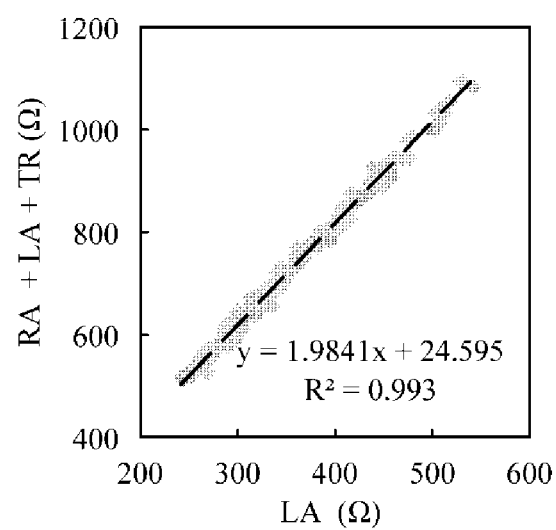

FIGS. 4A to 4C are diagrams explaining an example of measuring bio-impedance of a half of an upper body according to an example embodiment.

Referring to FIG. 4A, the bio-impedance measuring apparatuses 100, 200, and 300 as illustrated in FIGS. 1 to 3 may measure bio-impedance by using the half of the upper body. For example, the half of the upper body may indicate a right half 41 or a left half 42 of the upper body based on a left-right symmetric point of the upper body, e.g., the solar plexus. The right half 41 of the upper body includes a neck, a right chest, a right abdomen, a right face, and a right hand 43, and the left half 42 of the upper body includes a neck, a left chest, a left abdomen, a left face, and a left hand 44.

FIG. 4B illustrates a correlation between an impedance (right arm (RA)+left arm (LA)+trunk (TR)) of the upper body and an impedance (RA) of the right half of the upper body, and FIG. 4C illustrates a correlation between an impedance (RA+LA+TR) of the upper body and an impedance (LA) of the left half of the upper body. As illustrated in FIG. 4B, there is a high correlation of R=0.9928 between the impedance (RA) of the right half of the upper body and the impedance (RA+LA+TR) of the upper body, and as illustrated in FIG. 4C, there is a high correlation of $R^2=0.993$ between the impedance (LA) of the left half of the upper body and the impedance (RA+LA+TR) of the upper body. Further, there is a high correlation between the impedance of the upper body and the impedance of the whole body, which leads to a high correlation between the impedance of the half of the upper body and the impedance of the whole body.

Referring to FIGS. 5A to 7C, various types of structures of the main body 110 of the bio-impedance measuring apparatuses 100, 200, and 300 as illustrated in FIGS. 1 to 3, and an arrangement of the first electrode part 120 and the second electrode part 130 according to each structure of the main body 110 according to example embodiments will be described below.

Figure 5A:
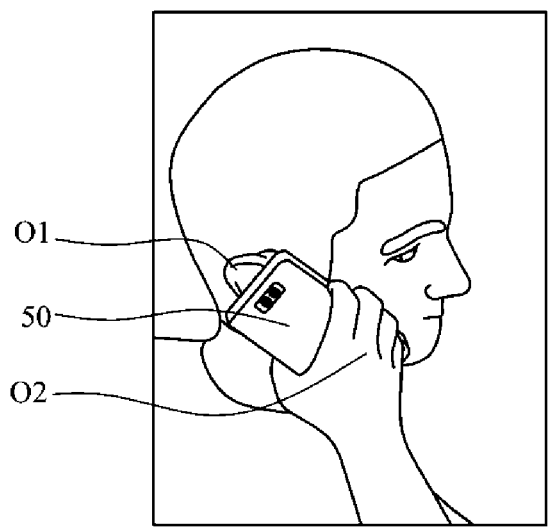
FIGS. 5A, 5B, 5C, and 5D are diagrams explaining bio-impedance measuring apparatuses of a mobile terminal type according to an example embodiment.

FIGS. 5A to 5D are diagrams explaining bio-impedance measuring apparatuses 100, 200, and 300 having a main body 50 of a mobile terminal type according to an example embodiment. Referring to FIG. 5A, bio-impedance may be measured while a user holds the main body 50 of the mobile terminal with one hand 02, and the mobile device 50 comes into contact with an ear 01 of the same half of the upper body as the hand 02 during a telephone conversation.

Figure 5B:
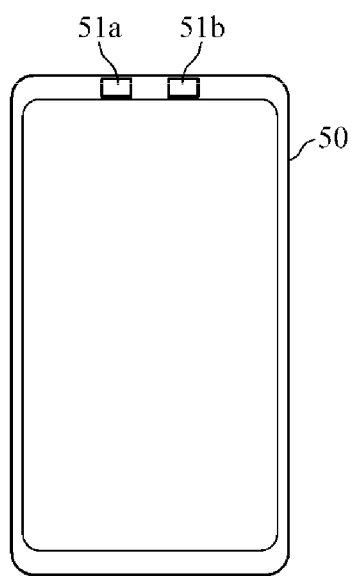

Referring to FIG. 5B, an input electrode 51a and an output electrode 51b of the first electrode part 120 may be disposed on a front surface of the main body 50 so that a first portion, e.g. an ear or a face, of the half of the upper body may come into contact with the input electrode 51a and the output electrode 51b of the first electrode part 120. As illustrated therein, the first electrode part 120 may be disposed on a bezel near a speaker at an upper front end of the main body 50. Alternatively, the first electrode part 120 may be provided as a transparent electrode on a front liquid crystal panel of the main body 50, or may be formed in a square shape on an edge of the speaker at the upper front end of the main body 50. But aspects of example embodiments are not limited thereto.

Figure 5C:
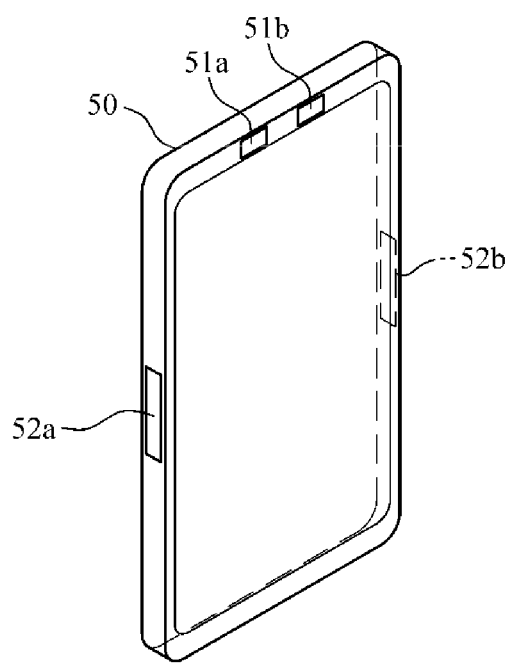
Figure 5D:
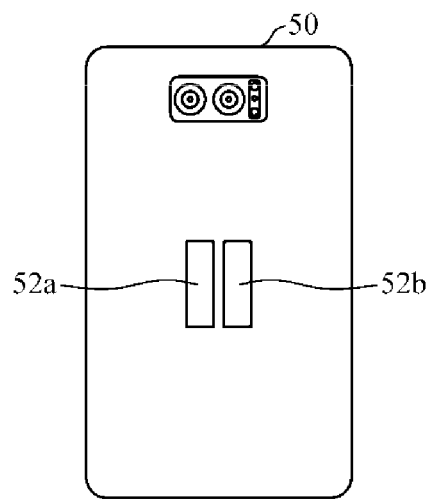

Referring to FIG. 5C, an input electrode 52a and an output electrode 52b of the second electrode part 130 may be disposed on both sides of the main body 50 so that a second portion, e.g., a finger, of the half of the upper body may come into contact the input electrode 52a and the output electrode 52b of the second electrode part 130. Alternatively, referring to FIG. 5D, the input electrode 52a and the output electrode 52b of the second electrode part 130 may be disposed on a rear surface of the main body 50 so that while a user holds the main body 50, the palm of the hand may come into contact with the input electrode 52a and the output electrode 52b of the second electrode part 130. But aspects of example embodiments are not limited thereto.

In this case, an impedance of the left half of the upper body may be measured while a user holds the main body 50 of the mobile terminal with the left hand, and the main body 50 is in contact with a left ear, and an impedance of the right half of the upper body may be measured while a user holds the main body 50 of the mobile terminal with the right hand, and the main body 50 is in contact with a right ear.

The measurer 140 is mounted in the main body 50 of a mobile terminal type. When the first electrode part 120 of the main body 50 of the mobile terminal comes into contact with the ear or the face, and the second electrode part 130 thereof comes into contact the hand, an internal and external power sources of the main body 50 may apply a current to the input electrodes 51a and 52a of the first electrode part 120 and the second electrode part 130. Further, the measurer 140 may measure a bio-impedance of the half of the upper body by measuring a voltage between both ends of the output electrodes of the first electrode part 120 and the second electrode part 130.

The display 210 is disposed on the front surface of the main body 50 of the mobile terminal in such a manner that the display 210 is exposed to the outside, and may include a touch panel. The display 210 may display guide information to enable the first electrode part 120 and the second electrode part 130 to more accurately contact the first portion (e.g., ear) and the second portion (e.g., hand). For example, the display 210 may display an arrow which indicates a position of the first electrode part 120 and the second electrode part 130. Further, the display 210 may output information showing that the first portion to touch the first electrode part 110 is the left ear, and a second portion to touch the second electrode part 120 is the left hand. In addition, the display 210 may output the bio-impedance measured by the measurer 140.

Moreover, the communicator 310 may be mounted in the main body 50 of the mobile terminal, and may be configured to transmit the measured bio-impedance to a user or a health monitoring device of a medical institution.

Further, a local impedance (e.g., impedance of an upper arm) may be measured in such a manner that while a user holds the main body 50 of the mobile terminal and is in contact with the second electrode part 130, an impedance is measured by touching the first electrode part 120 with a first portion (e.g., wrist) and a second portion (e.g., the inside of the elbow), sequentially.

Figure 6A:
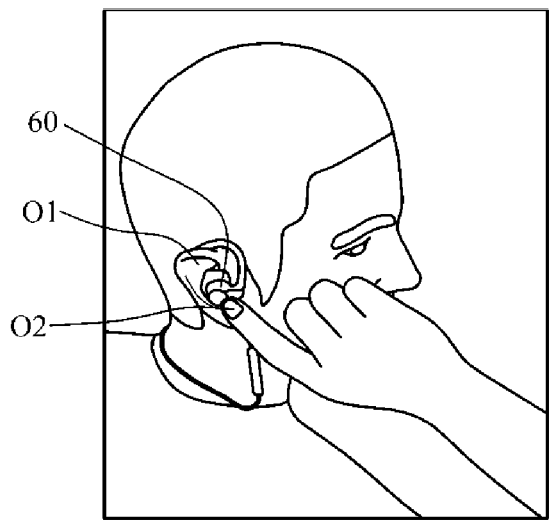
FIGS. 6A, 6B, 6C, 6D, and 6E are diagrams illustrating bio-impedance measuring apparatuses of an earphone type according to an example embodiment.

FIGS. 6A to 6E are diagrams illustrating the bio-impedance measuring apparatuses 100, 200, and 300 having main bodies 60 of various types of earphones according to an example embodiment. Referring to FIG. 6A, bio-impedance may be measured while, for example, a user listens to music by inserting a main body 60 of an earphone type into an ear 01, and touching the main body 60 with a finger 02.

Figure 6B:
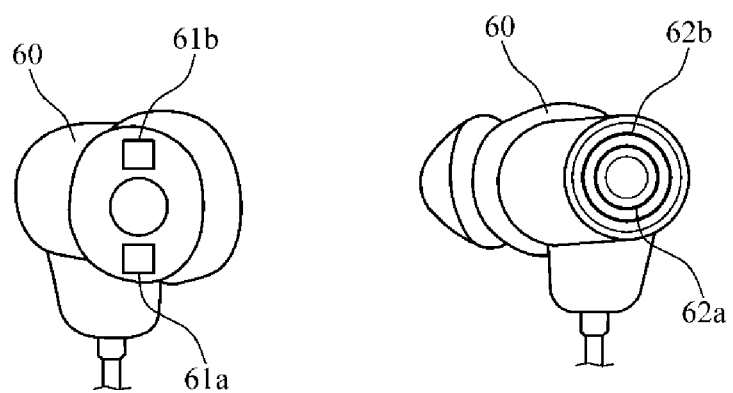

Referring to FIG. 6B, an input electrode 61a and an output electrode 61b of the first electrode part 120 may be disposed on an inner side surface of the main body 60 to come into contact with the inside of the ear when the main body 60 is inserted into the ear. Further, an input electrode 62a and an output electrode 62b of the second electrode part 130 may be disposed on an outer side surface of the main body 60 to come into contact with a finger while the main body 60 of the earphones is inserted into the ear. As illustrated in FIG. 6B, the first electrode part 120 and the second electrode part 130 may be formed in a concentric circle shape, and may also be formed in various shapes, such as a bar shape, a semi-circular shape, a square shape, and the like, according to shapes of the outer side surface of the main body 60.

In this case, the first electrode part 120 and the second electrode part 130 may be disposed on both left and right main bodies 60 of the earphones, or may be disposed on any one side thereof. When a user touches the outer side surface of the left-side main body 60 of the earphones with a left finger, an impedance of the left half of the upper body may be measured on the left finger and the left ear. Further, when a user touches the right surface of the right-side main body 60 of the earphones with a right finger, an impedance of the right half of the upper body may be measured on the right finger and the right ear.

Figure 6C:
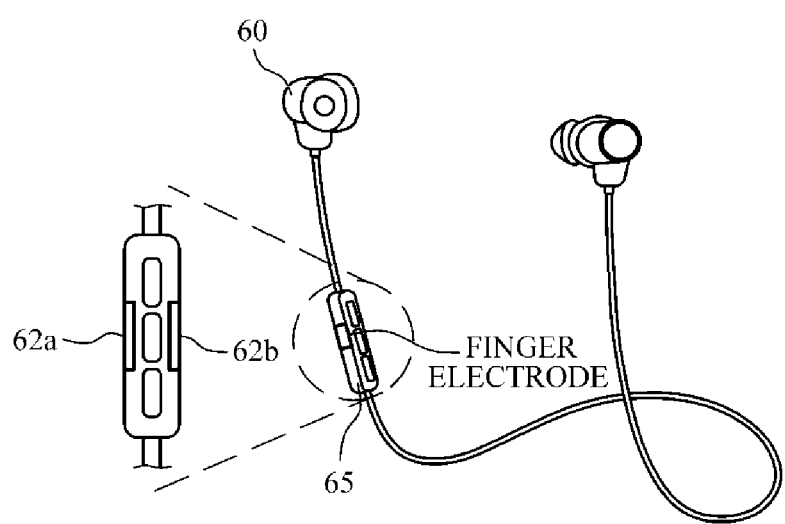

Referring to FIG. 6C, the second electrode part 130 may be disposed at an earphone controller 65 connected to the main body 60 of the earphones. In this case, the input electrode 62a and the output electrode 62b of the second electrode part 130 may be disposed on both sides of a function button of the controller 65, or may be disposed in a longitudinal direction of the controller 65.

In this case, the first electrode part 120 may be disposed on the inner side surface of the main body 60 on the side of the earphone where the earphone controller 65 is disposed. For example, when the earphone controller 65 is positioned on the right side, and when a user operates the earphone controller 65 with a right finger, an impedance of the right half of the upper body may be measured on the right ear and the right finger.

Figure 6D:
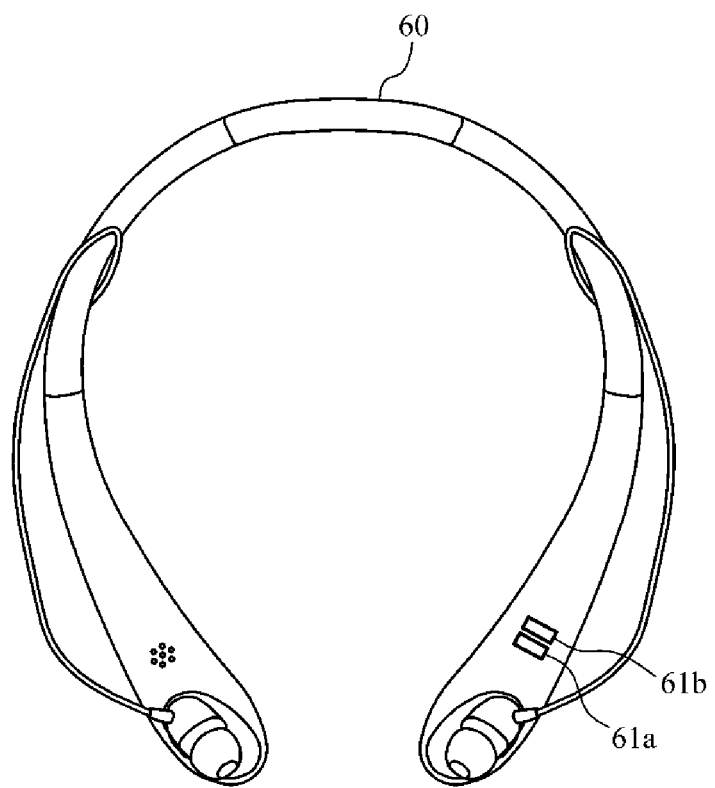

FIG. 6D illustrates a bio-information measuring apparatus of a neckband earphone type. As illustrated therein, the input electrode 61a and the output electrode 61b of the first electrode part 120 may be disposed on an inner side surface of a neckband to come into contact with a portion of the skin of the neck when a user wears the main body 60 of the earphones. In this case, the input electrode 62*a* and the output electrode 62*b* of the second electrode part 130 may be disposed on an outer side surface of a neckband or on an outer side surface of a portion where an ear cap is attached, so that the input electrode 62*a* and the output electrode 62*b* of the second electrode part 130 may come into contact with a finger of the same half of the upper body as the neck, which is contacted by the input electrode 61*a* and the output electrode 61*b* of the first electrode part 120.

Figure 6E:
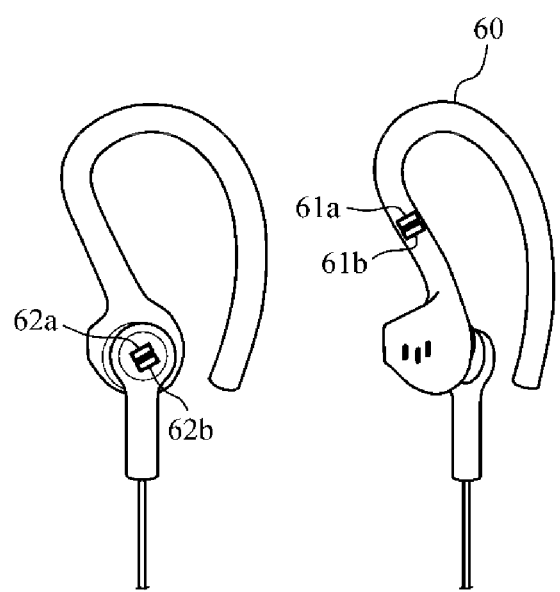

FIG. 6E is a diagram illustrating a main body 60 of earring-type earphones. As illustrated in FIG. 6E, the input electrode 61*a* and the output electrode 61*b* of the first electrode part 120 may be disposed on the inner side surface of a ring portion of the main body 60 of the earring-type earphones. In this case, the input electrode 62*a* and the output electrode 62*b* of the second electrode part 130 may be disposed at a predetermined position on the outer side of the main body 60, so the input electrode 62*a* and the output electrode 62*b* of the second electrode part 130 may come into contact with a finger of the same half of the upper body as the portion, which is in contact with the input electrode 61*a* and the output electrode 61*b* of the first electrode part 120.

The measurer 140 may be mounted in the main body 60 or the controller 65, and may supply a current to the input electrodes 61*a* and 62*a* of the first electrode part 120 and the second electrode part 130 by using the power of a battery mounted in the main body 60. Alternatively, in the case where the main body 60 of the earphones is connected to an external device, e.g., a mobile terminal, a wearable device, and the like, through a cable connector, the measurer 140 may supply a current to the input electrodes 61*a* and 62*a* by using the power of the external device.

The communicator 310 may be mounted in the main body 60 of the earphones, and may be connected to a mobile terminal, a wearable device, and the like through wired or wireless communications to transmit the measured bio-impedance to the mobile terminal or the wearable device, to output the measured bio-impedance or to analyze body composition.

A local impedance (e.g., impedance of an upper arm) may be measured by measuring an impedance when a user touches the first electrode part 120 of the main body 50 of the earphones with a first portion (e.g., wrist) of an object and touches the second electrode part 130 with a finger, and by measuring an impedance when a user touches the first electrode part 120 with a second portion (e.g., the inside of the elbow) and touches the second electrode part 130 with a finger.

Figure 7A:
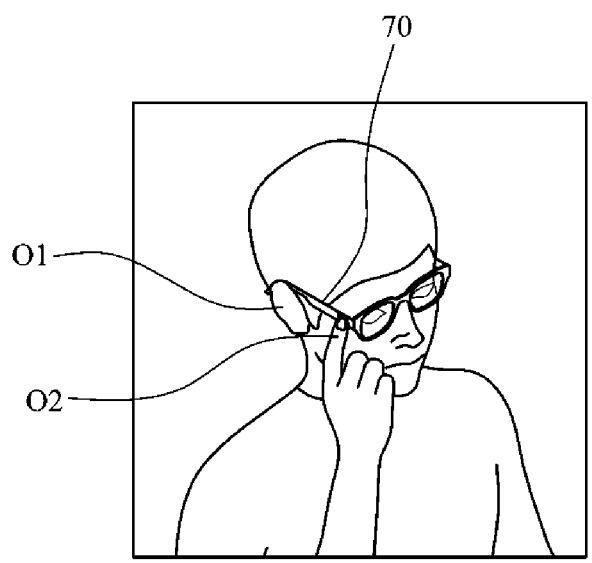
FIGS. 7A, 7B, and 7C are diagrams illustrating bio-impedance measuring apparatuses of a glasses type according to an example embodiment.
Figure 7B:
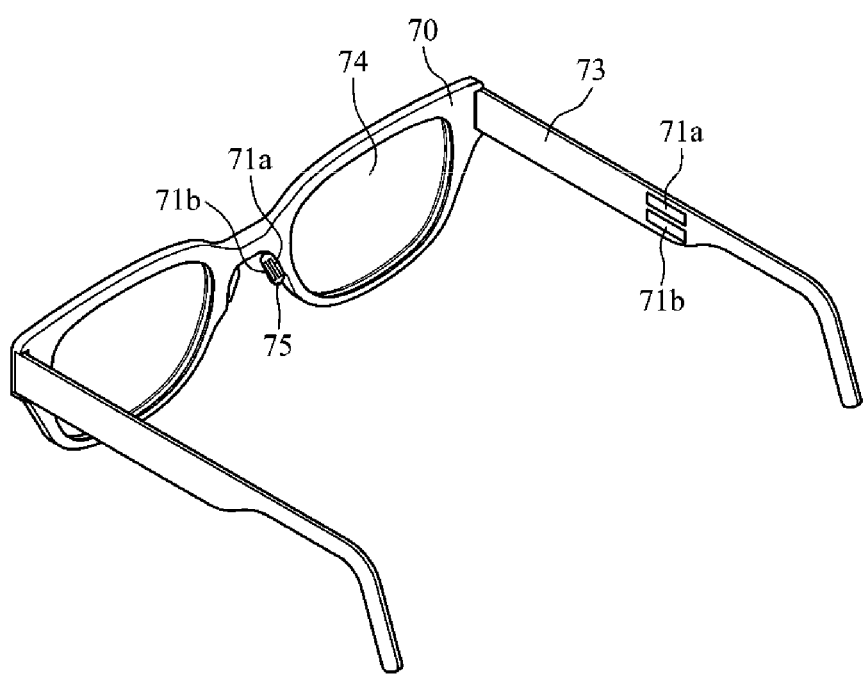
Figure 7C:
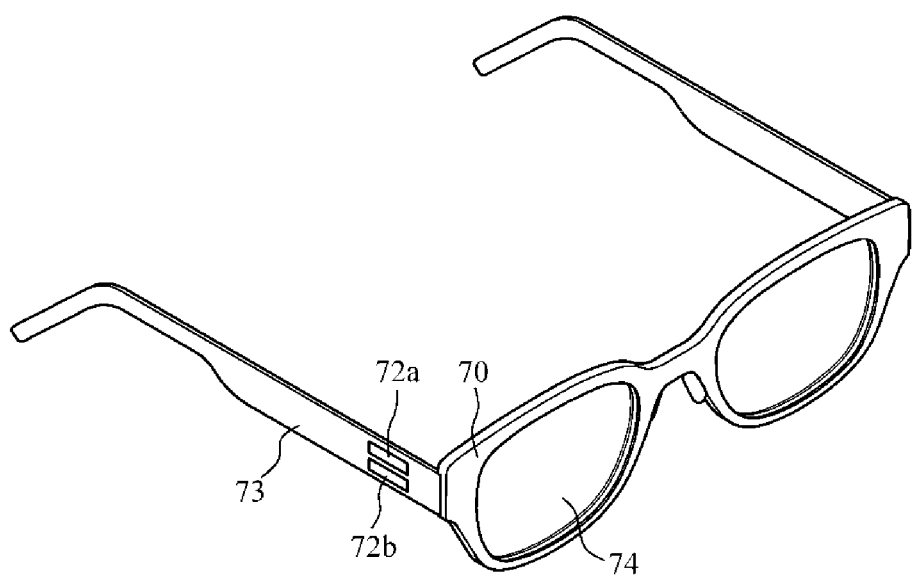

FIGS. 7A to 7C are diagrams illustrating bio-impedance measuring apparatuses 100, 200, and 300 having a main body 70 of different types of glasses. Referring to FIG. 7A, when a user touches the temples of glasses with a finger 02 while wearing glasses, an impedance of the half of the upper body may be measured.

Referring to FIG. 7B, an input electrode 71*a* and an output electrode 71*b* of the first electrode part 120 may be disposed on the inner surface of the temples 73 or a nose pad 75 of the main body 70, to come into contact with a face or an ear 01 of the half of the upper body. Further, referring to FIG. 7C, the input electrode 72*a* and the output electrode 72*b* of the second electrode part 130 may be disposed on an outer surface of the temples 73, to come into contact with a finger of a user. However, the arrangement of the input electrodes 71*a* and 72*a* and the output electrodes 71*b* and 72*b* are not limited thereto, and the input electrodes 71*a* and 72*a* and the output electrodes 71*b* and 72*b* may also be disposed at a position of the main body 70 which is mostly touched by fingers when a user adjusts glasses on the face.

In this case, the first electrode part 120 and the second electrode part 130 may be disposed at any one of a right-side temple or a left-side temple of glasses, so an impedance of the left half or the right half of the upper body may be measured, but the first electrode part 120 and the second electrode part 130 are not limited thereto, and may be disposed at both temples of glasses. While a user wears glasses and touches the second electrode part 130, disposed on the right temple 73 of the glasses, with a right finger, an impedance of the right half of the upper body may be measured. When a user touches the second electrode part 130, disposed on the left temple 73 of the glasses, with a left finger, an impedance of the left half of the upper body may be measured.

The measurer 140 may be mounted in the main body 70, e.g., in the temples of the glasses. The measurer 140 may apply a current to the input electrodes 71*a* and 72*a* of the first electrode part 120 and the second electrode part 130 by using power of an internal battery. Further, the measurer 140 may measure a bio-impedance of the half of the upper body by measuring a voltage on both ends of the output electrodes of the first electrode part 120 and the second electrode part 130.

The display 210 may be provided on glass 74 of the glasses. The display 210 may output the bio-impedance measured by the measurer 140.

Further, the communicator 310 may be mounted in the main body 70, and may be configured to transmit the measured bio-impedance to a mobile terminal, a wearable device, a health monitoring device of a medical institution, and the like.

Example embodiments of the bio-impedance measuring apparatuses 100, 200, and 300 having various types of main bodies, have been described above. However, the bio-impedance measuring apparatuses 100, 200, 300 are not limited thereto, and may be modified in various forms, such as a VR device, which may measure an impedance of the half of the upper body.

Figure 8:
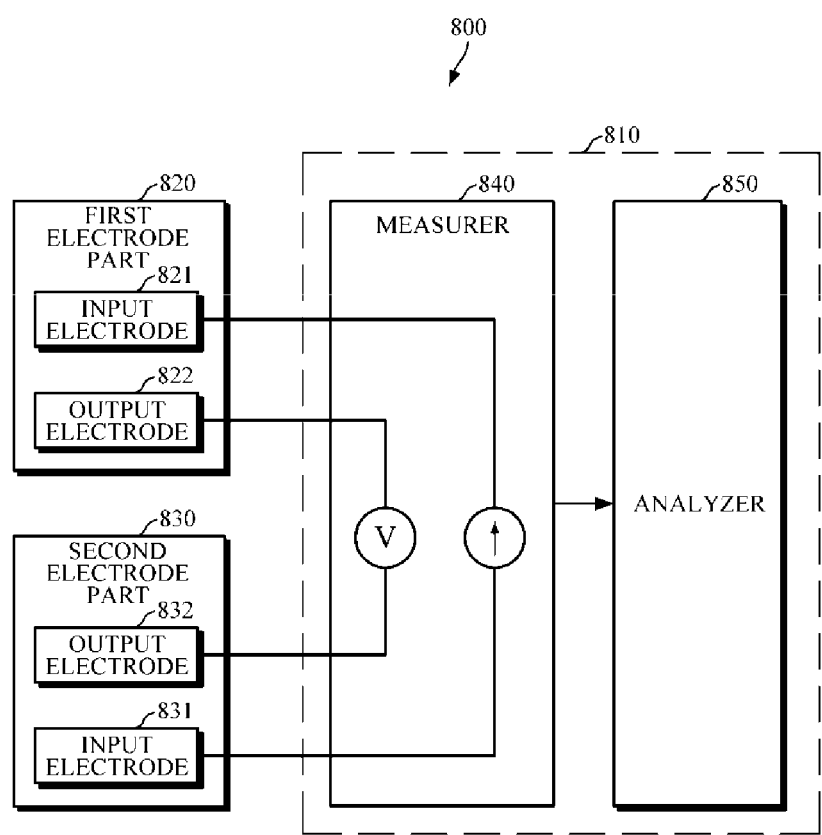
FIGS. 8, 9, and 10 are block diagrams illustrating examples of a body composition analyzing apparatus according to an example embodiment.
Figure 9:
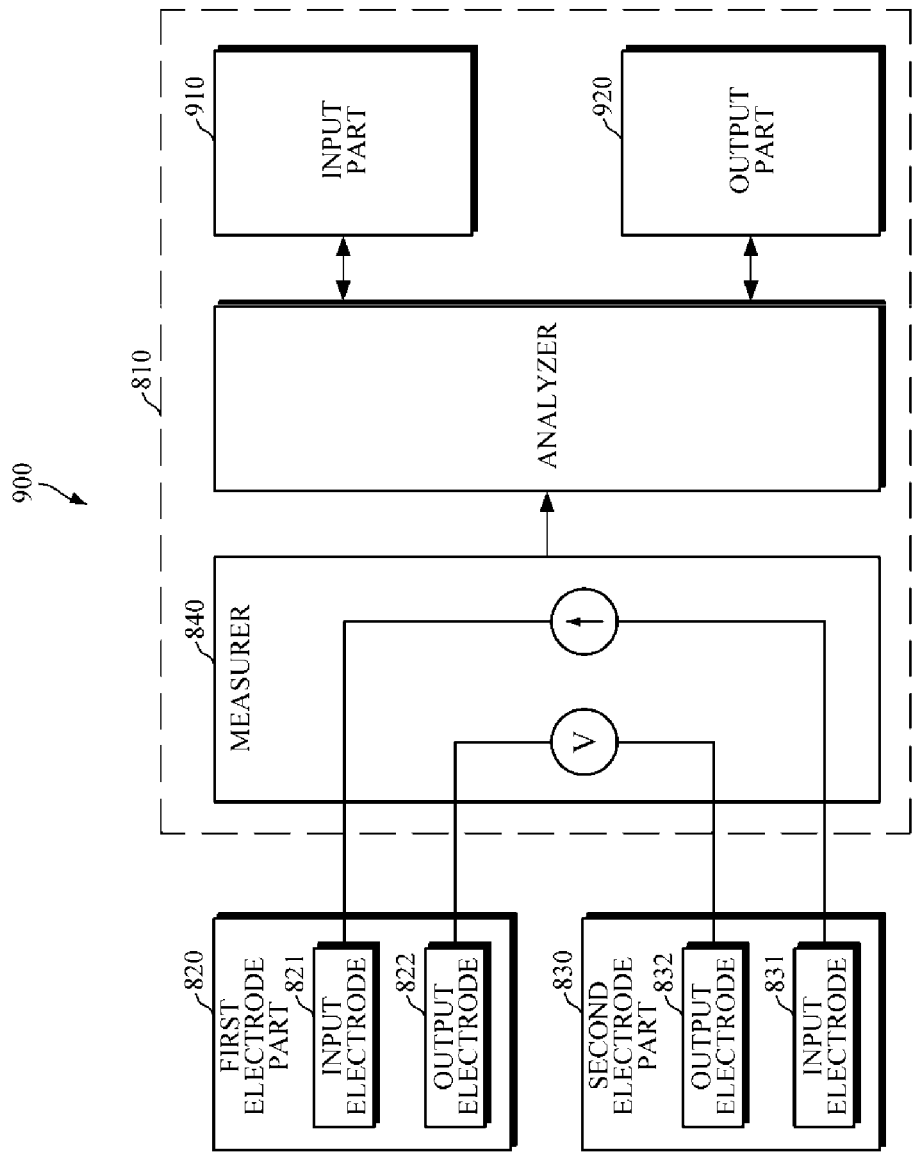
Figure 10:
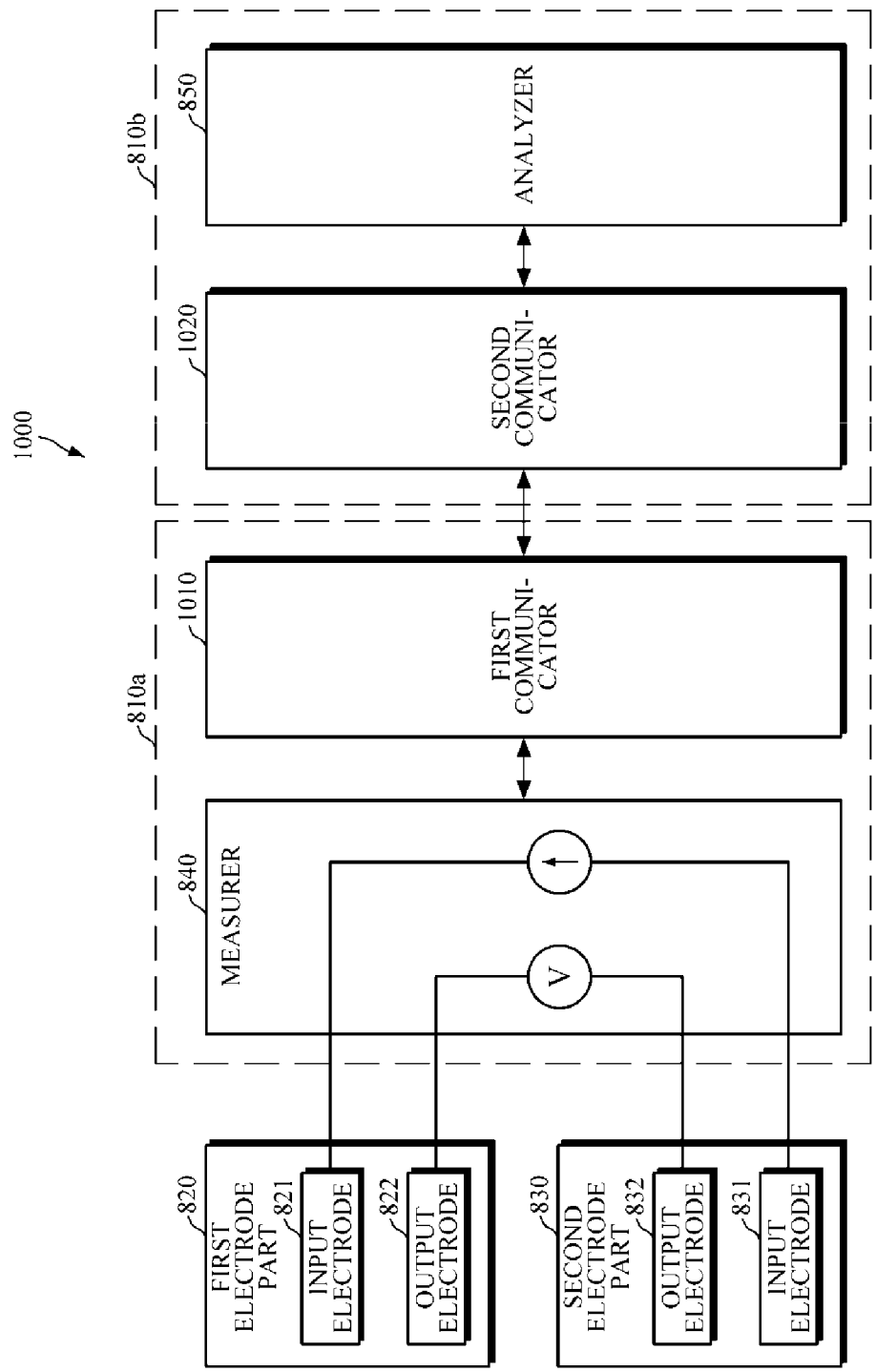

FIGS. 8 to 10 are block diagrams illustrating examples of a body composition analyzing apparatus.

Referring to FIG. 8, the body composition analyzing apparatus 800 includes a main body 810, a first electrode part 820, a second electrode part 830, a measurer 840, and an analyzer 850.

The body composition analyzing apparatus 800 may be implemented on various types of apparatuses. For example, as illustrated above with reference to FIGS. 5A to 7C, the main body 810 may include a mobile terminal type, a glasses type, an earphone type, and the like. In this case, in addition to modules to perform original functions of a mobile terminal, a glasses-type wearable device, or earphones, the main body 810 may include an analyzer 850 for analyzing body composition, in addition to the above-described parts for measuring a bio-impedance, such as the first electrode part 820, the second electrode part 830, and the measurer 840.

The first electrode part 820 and the second electrode part 830 may be mounted in the main body 810 in such a manner that the first electrode part 820 and the second electrode part 830 are exposed to the outside to come into contact with an object. The first electrode part 820 and the second electrode part 830 may measure a bio-impedance by using a two-electrode method or a four-electrode method. For example, in the case of measuring a bio-impedance by using the four-electrode method, the first electrode part 820 and the second electrode part 830 may include a pair of an input electrode 821 and an output electrode 822 and a pair of an input electrode 831 and an output electrode 832 respectively.

The input electrodes 821 and 831 and the output electrodes 822 and 832 may be formed in various shapes, such as a bar shape, a square shape, a circular shape, a semicircular shape, and the like. Further, according to a structure of the main body 810 and a position where the main body 810 is disposed, the input electrodes 821 and 831 and the output electrodes 822 and 832 may be formed in different shapes.

The first electrode part 820 and the second electrode part 830 may be disposed at a position of the main body 810 to more easily come into contact with portions of the same half of an upper body. For example, the first electrode 820 may be disposed on one surface of the main body 810 to easily come into contact with a face or an ear of the half of an upper body of an object, and the second electrode 830 may be disposed on the other surface of the main body 810 to come into contact with a hand, such as a finger or a palm of the hand, of the same half of the upper body which is contacted by the first electrode part 820. The arrangement of the first electrode part 820 and the second electrode part 830 according to various types of the main body 810 is described above with reference to FIGS. 5A to 7C.

The measurer 840, which is embedded in the main body 810, may apply a current to the input electrodes 821 and 831 of the first electrode part 820 and the second electrode part 830 which are in contact with an object, and may measure a bio-impedance by measuring a voltage between the output electrodes 822 and 832. The measurer 840 may supply a current by receiving power from a battery mounted in the main body 810, or from an external device connected to the main body 810.

The measurer 840 may measure an impedance of the half of the upper body in a region of the half of the upper body of an object, and may measure an impedance of the upper body or the whole body based on the measured impedance of the half of the upper body. As the upper body is left-right symmetric based on the solar plexus, the impedance of the upper body or the whole body may be measured by using the measured impedance of the half of the upper body.

The analyzer 850 may analyze body composition of a user based on the impedance of the half of the upper body which is measured by the measurer 840. In this case, the body composition of the user may include one or more of intracellular water, extracellular water, proteins, minerals, body fat, skeletal muscle mass, degree of obesity, muscle strength, edema, body composition ratio, visceral fat, body mass index (BMI), and skeletal mass index (SMI).

The analyzer 850 may analyze body composition of the left half and the right half of the upper body by using an impedance of the left half of the upper body and an impedance of the right half of the upper body which are measured on the left half and the right half of the upper body of a user, and may calculate a body balance index based on the analysis of the body composition of both halves of the upper body. In this case, the analyzer 850 may guide a user to first measure a bio-impedance of the left half of the upper body, and upon completing measurement of the left half of the upper body, the measurer 840 may then guide a user to measure a bio-impedance of the right half of the upper body.

Further, in addition to the function of analyzing body composition, the analyzer 850 may perform an additional function mounted in the main body 810, for example, monitoring a skin condition, or analyzing bio-information which includes blood pressure, vascular age, vascular age, vascular compliance, stress index, aortic pressure waveform, degree of fatigue, blood glucose, cholesterol, triglyceride, proteins, alcohol, and the like, by considering bio-signals received from sensors, such as an electrocardiogram (ECG) sensor, an electromyogram (EMG) sensor, a ballistocardiogram (BCG) sensor, a photoplethysmography (PPG) sensor, and the like.

The analyzer 850 may be embodied as various numbers of hardware, software and/or firmware structures that execute the above-described functions described above. For example, the analyzer 850 may use a direct circuit structure, such as a memory, a processor, a logic circuit, a look-up table, etc. that may execute the above-described functions through controls of one or more microprocessors or other control apparatuses. Also, the analyzer 850 may be specifically embodied by a module, a program, or a part of code, which contains one or more executable instructions for performing specified logic functions, and executed by one or more microprocessors or other control apparatuses. The analyzer 850 may further include or may be implemented by a processor such as a central processing unit (CPU) that performs the above-described functions, a microprocessor, or the like. Further, although a bus is not illustrated in FIG. 8, communications between the analyzer 850 and the measurer 840 may be performed through the bus.

Referring to FIG. 9, the body composition analyzing apparatus 900 may further include an input part 910 and an output part 920, in addition to the main body 810, the first electrode part 820, the second electrode part 830, the measurer 840, and the analyzer 850. The main body 810, the first electrode part 820, the second electrode part 830, the measurer 840, and the analyzer 850 are described above with reference to FIG. 8.

The main body 810 may be formed in one physical structure. For example, the main body 810 may be a mobile terminal type, a glasses type, an earphone type, and the like; and in addition to the first electrode part 820, the second electrode part 830, the measurer 840, and the analyzer 850, which are provided form measuring body composition, and the input part 910 and the output part 920, the main body 810 may include modules, which are appropriate for the structure of the main body 810, to perform their original functions.

The input part 910 may include an interface such as a user interface for interaction with a user. The input part 910 may receive various commands or information input by a user through the user interface. The input part 910 may receive input of user information including sex, age, height, and weight of a user.

Once the measurer 840 measures an impedance of the half of the upper body, the analyzer 850 may analyze body composition based on the measured impedance of the half of the upper part, and the user information which is input through the input part 910.

The output part 920 may output the impedance of the half of the upper part which is measured by the measurer 840, the analysis of body composition of the analyzer 850, a body balance index, and the like. The output part 920 may include at least one of a display module, a speaker module, a haptic module, and the like according to the structure of the main body 810. The output part 920 may output the measured bio-impedance or the analysis of body composition by using various visual methods. Alternatively, the output part 920 may output the information in voice through a speaker module, and may provide additional information, such as a warning, through vibration, tactility, and the like, through a haptic module.

The output part 920 may display an outline of the half of the upper body, of which the impedance is measured, and may display a contact position of each of the electrode parts 820 and 830 on the outline of the half of the upper body.

Referring to FIG. 10, the body composition analyzing apparatus 1000 may include two or more main bodies 810a and 810b, a first electrode part 820, a second electrode part 830, a measurer 840, an analyzer 850, a first communicator 1010, and a second communicator 1020. The first electrode part 820, the second electrode part 830, the measurer 140, and the analyzer 850 are described above with reference to FIGS. 8 and 9.

In an example embodiment, the body composition analyzing apparatus 1000 may have a structure of two or more main bodies 810a and 810b. The first main body 810a may include modules to measure bio-impedance of the half of the upper body, and the second main body 810b may include modules to analyze body composition by using the measured bio-impedance.

For example, as illustrated in FIGS. 6A to 7C, the first main body 810a may be provided as an earphone type or a glasses type, to perform functions of earphones or a glasses-type wearable device. Further, as illustrated in FIGS. 5A to 5D, the second main body 810b may be provided as a mobile terminal, such as a smartphone or a table PC, or a wrist-type wearable device, to perform functions of a mobile terminal or a wrist-type wearable device. In this manner, the first main body 810a and the second main body 810b may perform their respective functions independently from each other, while collaborating with each other by sharing some functions of analyzing body composition.

The first main body 810a may include the measurer 840 for measuring a bio-impedance, and the first communicator 1010 for communicating with modules mounted in the second main body 810b. The input electrodes 821 and 831 and the output electrodes 822 and 832 of the first electrode part 820 and the second electrode part 830 may be disposed at positions according to various types of the first main body 810a.

The measurer 840 may measure bio-impedance of the half of the upper body, and may transmit the measured bio-impedance of the half of the upper body through the communicator 1010 to the analyzer 850 mounted in the second main body 810b.

The second main body 810b may include the analyzer 850 for analyzing body composition, and the second communicator 1020 for communicating with modules mounted in the first main body 810a.

The analyzer 850 may transmit a request for measuring bio-impedance to the measurer 840 via the first communicator 1010 in the first main body 810a through the second communicator 1020. The analyzer 850 may analyze body composition based on the impedance of the half of the upper body which is received from the measurer 840.

The first communicator 1010 and the second communicator 1020 may perform wired communication through a wired connector, or may perform wireless communication by using the above-described various wireless communication techniques.

Figure 11:
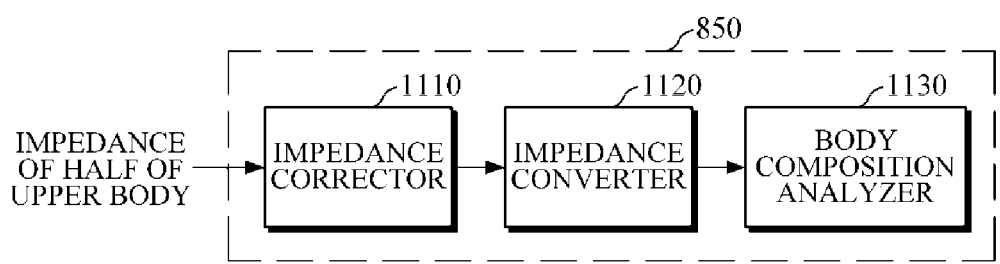
FIG. 11 is a block diagram illustrating an analyzer of body composition analyzing apparatuses according to an example embodiment.

FIG. 11 is a block diagram illustrating an analyzer 850 of body composition analyzing apparatuses 800, 900, and 1000 according to the example embodiments of FIGS. 8 to 10.

Referring to FIG. 11, the analyzer 850 of the body composition analyzing apparatuses 800, 900, and 1000 includes an impedance corrector 1110, an impedance converter 1120, and a body composition analyzer 1130.

Upon receiving an impedance of the half of the upper body from the measurer 840, the impedance corrector 1110 may correct the received impedance of the half of the upper body to be appropriate for analysis of body composition. For example, in the case where an impedance of the half of the upper body is measured by touching the first electrode 820 with an ear, and an impedance of the half of the upper body is measured by touching the second electrode 830 with a finger, the measured impedance of the half of the upper body may include a face impedance of and a neck impedance.

The impedance corrector 1110 may remove the face impedance and the neck impedance from the measured impedance of the half of the upper body. Generally, since an impedance of the whole body or an impedance of the half of the upper body does not include the face impedance or the neck impedance, the impedance corrector 1110 may remove an additional impedance, such as a face impedance, a neck impedance, a finger impedance, and the like, based on a pre-stored impedance of the whole body or the half of the upper body.

The impedance corrector 1110 may update the impedance of the whole body or the half of the upper body, which is a reference for correction, according to analysis of the corrected impedance, a predetermined update cycle, a user's request, and the like. In this case, the impedance corrector 1110 may control a mounted communication module to communicate with an external device, e.g., a device for measuring an impedance of the whole body or an impedance of the upper body, and may update the impedance of the whole body or the impedance of the upper body of a user which are measured by the device for measuring the impedance of the whole body or the impedance of the upper body.

Once the impedance of the half of the upper body is corrected by the impedance corrector 1110, the impedance converter 1120 may convert the corrected impedance of the half of the upper body into a predetermined form. In this case, the predetermined form may include a linear expression (e.g., constant×Z), a fractional expression (e.g., constant/Z), an exponential expression (e.g., constant×$Z^a$), and the like, and may be pre-defined in an appropriate form for each user, in which Z denotes a corrected impedance of the half of the upper body, and a is any constant.

The body composition analyzer 1130 may analyze body composition based on user information including the converted impedance, sex, age, height, weight, and the like. For example, body fat may be calculated by using a multiple regression equation such as the following Equation 1.

$$BF = a_0 + a_1 \times S + a_2 \times A + a_3 \times H + a_4 \times W + a_5 \times H^2/Z_{RA} \quad \text{[Equation 1]}$$

Herein, BF denotes body fat percentage (%), S denotes sex, A denotes age, H denotes height, and W denotes weight. $Z_{RA}$ denotes the right half of the upper body, and may be an impedance after correction, from which the face impedance and the neck impedance are removed. Further, $a_0$, $a_1$, $a_2$, $a_3$, $a_4$, $a_5$, which are constants, are example weighted values applied to elements such as sex, age, height, weight, and the like.

Figure 12:
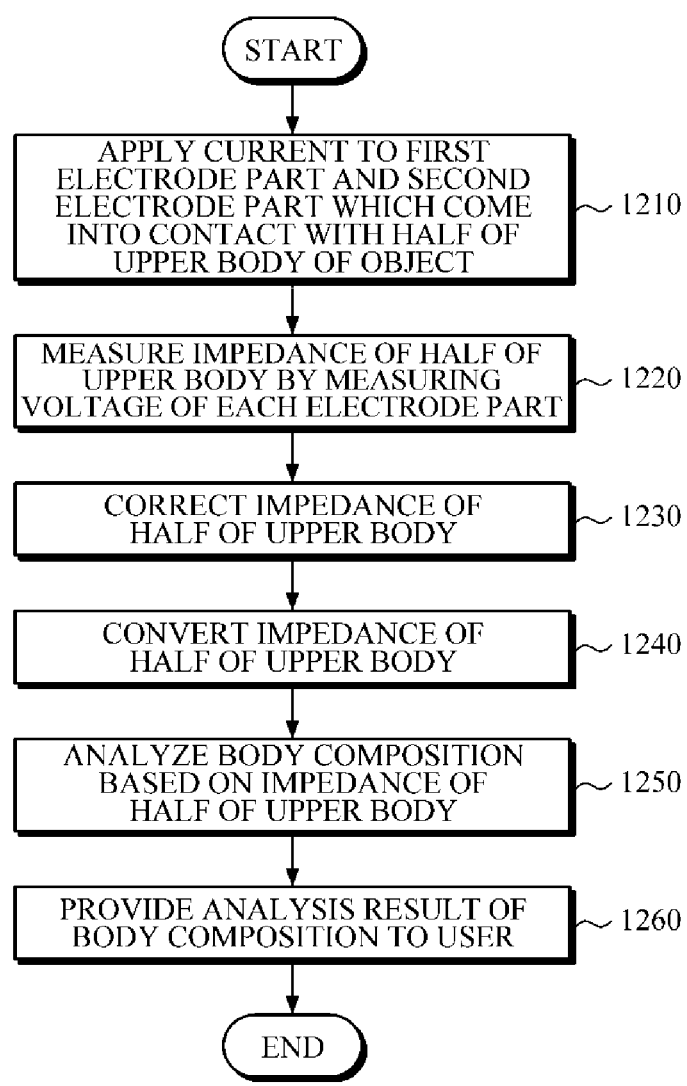
FIG. 12 is a flowchart illustrating an example of a body composition analyzing method according to an example embodiment.

FIG. 12 is a flowchart illustrating an example of a body composition analyzing method according to an ex ample embodiment.

FIG. 12 may be an example of a body composition analyzing method performed by the body composition analyzing apparatuses 800, 900, and 1000 of FIGS. 8 to 10.

Upon receiving a request for analyzing body composition, the body composition analyzing apparatus may apply a current to the first electrode part and the second electrode part which come into contact with the half of the upper part of an object in 1210. In this case, the current may be an alternating current, and the alternating current may be a constant current of, for example, about 500µ having a frequency of 50 kHz, and the first electrode part and the second electrode part may use any one of a two-electrode method or a four-electrode method. The first electrode part and the second electrode part may be disposed at positions of the main body to respectively contact, for example, an ear or a face and a finger.

Then, the body composition analyzing apparatus may measure an impedance of the half of the upper body by measuring a voltage between both ends of each electrode pail in 1220.

Subsequently, the body composition analyzing apparatus may correct the impedance of the half of the upper body for analysis of body composition in 1230. For example, in the case where the impedance of the half of the upper body is an impedance of the half of the upper body which is measured on an ear and a finger, the measured impedance of the half of the upper body may include a face impedance or a neck impedance. Generally, since an impedance of the whole body or an impedance of the half of the upper body does not include the face impedance or the neck impedance, the body composition analyzing apparatus may remove an additional impedance, such as a face impedance, a neck impedance, a finger impedance, and the like, from the measured impedance of the half of the upper body based on an impedance of the whole body or an impedance of the upper body which is pre-stored for each user.

Next, upon correcting the impedance of the half of the upper body in 1230, the body composition analyzing apparatus may convert the corrected impedance (Z) of the half of the upper body into a predetermined form such as a linear expression (e.g., constant×Z), a fractional expression (e.g., constant/Z), an exponential expression (e.g., constant×$Z^a$), and the like in 1240.

Then, the body composition analyzing apparatus may analyze body composition based on the converted impedance, and the user information including sex, age, height, weight, and the like in 1250. In this case, upon measuring an impedance of the left half of the upper body and an impedance of the right half of the upper body of a user, the body composition analyzing apparatus may calculate a left-right balance index of a human body. Further, the body composition analyzing apparatus may calculate additional information, such as skin monitoring information and the like, based on the analysis of body composition.

Subsequently, the body composition analyzing apparatus may provide an analysis result of body composition to a user in 1260. In this case, the body composition analyzing apparatus may output the information by various methods using a display module, a speaker module, a haptic module, and the like.

The present invention can be realized as a computer-readable code written on a computer-readable recording medium. The computer-readable recording medium may be any type of recording device in which data is stored in a computer-readable manner.

Examples of the computer-readable recording medium include a read-only memory (ROM), a random-access memory (RAM), a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing the present disclosure may be deduced by one of ordinary skill in the art.

While one or more example embodiments have been described with reference to the figures, it will be understood by those of ordinary skill in the art that various changes in form and details may be made therein without departing from the spirit and scope as defined by the following claims.

What is claimed is:

1. A body composition analyzing apparatus comprising:
   a first electrode pair configured to come into contact with a first portion of a half of an upper body of a human, the half of the upper body of the human being one of a left half of the upper body of the human or a right half of the upper body of the human, the first portion being at least one of a face, an ear, a nose, and a neck of the half of the upper body of the human;
   a second electrode pair configured to come into contact with a second portion of the half of the upper body, the second portion being a hand of the half of the upper body of the human; and
   at least one processor configured to:
   apply a current to the first electrode pair and the second electrode pair;
   measure an impedance of the first portion of the half of the upper body of the human and the second portion of the half of the upper body of the human based on measuring a voltage of the first electrode pair and the second electrode pair, respectively;
   analyze body composition of the human based on the measured impedance of the half of the upper body; and
   correct the measured impedance of the half of the upper body of the human by removing at least one measured impedance of the first portion based on at least one of an impedance of a whole body of the human and an impedance of the upper body of the human, and analyze the body composition based on the corrected impedance.

2. The body composition analyzing apparatus of claim 1, wherein the left half of the upper body of the human or the right half of the upper body of the human is based on a left-right symmetric point of the upper body of the human.

3. The body composition analyzing apparatus of claim 1, wherein the first electrode pair is further configured to come into contact with the at least one of the face, the ear, the nose, and the neck of the half of the upper body of the human, and the second electrode pair is further configured to come into contact with the hand of the half of the upper body of the human.

4. The body composition analyzing apparatus of claim 3, further comprising a main body, the main body being a mobile terminal,
   wherein the first electrode pair is disposed on a front surface of the mobile terminal, and the second electrode pair is disposed on a side surface or a rear surface of the mobile terminal.

5. The body composition analyzing apparatus of claim 3, further comprising a main body, the main body being an earphone,
   wherein the first electrode pair is disposed on an inner side surface of ,a neckband of the earphone which is configured to come into contact with the ear or the neck, or disposed on an inner side surface of an earbud of the earphone which is configured to be inserted into the ear, and
   wherein the second electrode pair is disposed on an outer side surface of the neckband or the earbud which is exposed to the outside, or disposed at a controller of the earphone connected to the neckband or the earbud of the earphone.

6. The body composition analyzing apparatus of claim 3, further comprising a main body, the main body being glasses,
wherein the first electrode pair is disposed on an inner surface of a nose pad or temples of the glasses and is further configured to come into contact with at least one of the nose, the ear, and the face of the half of the upper body of the human, and the second electrode pair is disposed on an outer surface of the glasses and is further configured to come into contact with the hand of the half of the upper body of the human.

7. The body composition analyzing apparatus of claim 1, further comprising an input interface configured to receive a user input of user information comprising at least one of sex, age, height, and weight of the human.

8. The body composition analyzing apparatus of claim 7, wherein the at least one processor is further configured to analyze the body composition based on the user information and the measured impedance of the half of the upper body of the human.

9. The body composition analyzing apparatus of claim 8, wherein the impedance of the whole body of the human and the impedance of the upper body of the human is stored in a storage.

10. The body composition analyzing apparatus of claim 1, wherein the at least one processor is further configured to convert the measured impedance of the half of the upper body of the human into at least one of a linear expression, a fractional expression, and an exponential expression, and to analyze the body composition based on the converted impedance.

11. The body composition analyzing apparatus of claim 1, wherein the at least one processor is further configured to calculate a body balance index by comparing an analysis result of body composition of a left half of the upper body of the human with an analysis result of body composition of a right half of the upper body of the human.

12. The body composition analyzing apparatus of claim 1, wherein the body composition comprises at least one of intracellular water, extracellular water, proteins, minerals, a body fat, a skeletal muscle mass, a degree of obesity, a muscle strength, an edema, a body composition ratio, a visceral fat, a body mass index (BMD, and a skeletal mass index (SMI).

13. The body composition analyzing apparatus of claim 1, further comprising an output part configured to output at least one of the measured impedance of the half of the upper body of the human and an analysis result of the body composition.

14. A body composition analyzing method comprising:
applying a current to a first electrode pair and a second electrode pair which are configured to come into contact with a first portion and a second portion of a half of an upper body of an human, respectively, the half of the upper body of the human being one of a left half of the upper body of the human or a right half of the upper body of the human, the first portion being at least one of a face, an ear, a nose, and a neck of the half of the upper body of the human and the second portion being a hand of the half of the upper body of the human;
measuring an impedance of the first portion of the half of the upper body of the human and the second portion of the half of the upper body of the human based on a voltage measured of the first electrode pair and the second electrode pair, respectively; and
analyzing body composition of the human based on the measured impedance of the half of the upper body of the human,
wherein the analyzing of the body composition further comprises correcting the measured impedance of the half of the upper body of the human by removing at least one measured impedance of the first portion that is included in the half of the upper body of the human based on at least one of an impedance of a whole body of the human and an impedance of the upper body of the human, and analyzing the body composition based on the corrected impedance.

15. The body composition analyzing method of claim 14, wherein the first electrode pair is further configured to come into contact with the at least one of the face, the ear, the nose, and athe neck of the half of the upper body of the human, and the second electrode pair is configured to come into contact with the hand of the half of the upper body of the human.

16. The body composition analyzing method of claim 14, wherein the analyzing of the body composition further comprises analyzing the body composition based on user information comprising at least one of sex, age, height, and weight of the human, and the measured impedance of the half of the upper body of the human.

17. The body composition analyzing method of claim 14, wherein the impedance of the whole body of the human and the impedance of the upper body of the human is stored in a storage.

18. The body composition analyzing method of claim 14, further comprising outputting at least one of the measured impedance of the half of the upper body of the human and an analysis result of the body composition.

19. A bio-impedance measuring apparatus comprising:
a main body;
a first electrode pair which is disposed in the main body and is configured to come into contact with a first portion of a half of an upper body of an human, the half of the upper body of the human being one of a left half of the upper body of the human and a right half of the upper body of the human, the first portion being at least one of a face, an ear, a nose, and a neck of the half of the upper body of the human;
a second electrode pair which is disposed in the main body and is configured to come into contact with a second portion of the half of the upper body of the human, the second portion being a hand of the half of the upper body of the human; and
at least one processor which is disposed in the main body and is configured to:
apply a current to the first electrode pair and the second electrode pair,
measure an impedance of the first portion of the half of the upper body of the human and the second portion of the half of the upper body of the human based on measuring a voltage of the first electrode pair and the second electrode pair, respectively, and
correct the measured impedance of the half of the upper body of the human by removing at least one measured impedance of the first portion that is included in the half of the upper body of the human based on at least one of an impedance of a whole body of the human and an impedance of the upper body of the human, and analyze body composition based on the corrected impedance.

20. The bio-impedance measuring apparatus of claim 19, wherein each of the first electrode pair and the second electrode pair comprises an input electrode, to which the current is applied, and an output electrode configured to output the voltage.

21. The bio-impedance measuring apparatus of claim 20, wherein the input electrode and the output electrode are formed in at least one of a bar shape, a semi-circular shape, and a circular shape.

22. The bio-impedance measuring apparatus of claim 19, wherein the left half of the upper body of the human or the right half of the upper body of the human is based on a left-right symmetric point of the upper both of the human.

23. The bio-impedance measuring apparatus of claim 19, wherein the main body is a mobile terminal, and
wherein the first electrode pair is disposed on a front surface of the mobile terminal and is further configured to come into contact with the face or the ear of the half of the upper body of the human, and the second electrode pair is disposed on a side surface or a rear surface of the main body and is further configured to come into contact with the hand of the half of the upper body of the human.

24. The bio-impedance measuring apparatus of claim 23, further comprising a display disposed in the main body and configured to display a measurement result of a bio-impedance.

25. The bio-impedance measuring apparatus of claim 19, wherein the main body is an earphone,
wherein the first electrode pair is disposed on an inner side surface of a neckband of the earphone configured to come into contact with the ear or the neck of the half of the upper body of the human, or disposed on an inner side surface of an earbud of the earphone configured to be inserted into the ear of the half of the upper body of the human, and
wherein the second electrode pair is disposed on an outer side surface of the neckband or the earbud of the earphone which is exposed to the outside, or disposed at a controller of the earphone connected to the neckband or the earbud of the earphone to come into contact with the hand of the half of the upper body of the human.

26. The bio-impedance measuring apparatus of claim 25, wherein when connected by wire to an external device, the at least one processor applies the current to the first electrode pair and the second electrode pair by receiving power from the external device.

27. The bio-impedance measuring apparatus of claim 25, further comprising a communicator configured to transmit one or more of the measured voltage and the measured bio-impedance to an external device through wired or wireless communication.

28. The bio-impedance measuring apparatus of claim 19, wherein the main body is glasses, and
wherein the first electrode pair is disposed on an inner surface of a nose pad or temples of the glasses and is further configured to come into contact with the at least one of the nose, the ear, and the face of the half of the upper body of the human, and the second electrode pair is disposed on an outer surface of the temples of the glasses and is further configured to come into contact with the hand of the half of the upper body of the human.

29. The bio-impedance measuring apparatus of claim 28, further comprising a display disposed on the main body and configured to display a measurement result of a bio-impedance.

30. The body composition analyzing apparatus of claim 1, wherein the first electrode pair comprises a first input electrode and a first output electrode, and the second electrode pair comprises a second input electrode and a second output electrode, and
wherein the at least one processor is further configured to apply the current to each of the first input electrode and the second input electrode, and to measure the voltage between the first output electrode and the second output electrode.

31. The body composition analyzing apparatus of claim 13, wherein the output part comprises at least one of a display, a speaker, and a haptic module.

32. The body composition analyzing method of claim 17, where in the analyzing of the body composition further comprises converting the corrected impedance of the half of the upper body of the human into at least one of a linear expression, a fractional expression, and an exponential expression, and analyzing the body composition based on the converted impedance.

33. A bio-impedance measuring apparatus comprising:
a main body;
a first electrode pair which is disposed in the main body and is configured to come into contact with a first portion of a half of an upper body of a human, the half the of the upper body of the human being one of a left half of the upper body of the human and a right half of the upper body of the human, the first portion being at least one of a face, an ear, a nose, and a neck of the half of the upper body of the human;
a second electrode pair which is disposed in the main body and is configured to come into contact with a second portion of the half of the upper body of the human, the second portion being a hand of the half of the upper body of the human;
at least one processor which is disposed in the main body, the at least one processor being configured to:
apply a current to the first electrode pair and the second electrode pair, and to measure an impedance of the first portion of the half of the upper body of the human and the second portion of the half of the upper body of the human based on measuring a voltage of first electrode pair and the second electrode pair, respectively;
correct the measured impedance of the half of the upper body by removing at least one measured impedance of the first portion that is included in the half of the upper body of the human based on at least one of an impedance of a whole body of the human and an impedance of the upper body of the human, and
convert the corrected impedance of the of the half of the upper body of the human into at least one of a linear expression, a fractional expression, and an exponential expression, and to analyze body composition based on the converted impedance.

* * * * *